US011466187B2

(12) United States Patent
Lipscomb et al.

(10) Patent No.: US 11,466,187 B2
(45) Date of Patent: Oct. 11, 2022

(54) COMPOSITION CONTAINING A SILICONE-BASED ADHESIVE AND CELLULOSE NANOCRYSTALS, AND METHODS AND ARTICLES

(71) Applicant: 3M INNOVATIVE PROPERTIES COMPANY, St. Paul, MN (US)

(72) Inventors: Corinne E. Lipscomb, St. Paul, MN (US); Kiu-Yuen Tse, Woodbury, MN (US); Jenna L. Richardson, St. Paul, MN (US); Karl E. Benson, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 318 days.

(21) Appl. No.: 16/646,295

(22) PCT Filed: Oct. 17, 2018

(86) PCT No.: PCT/IB2018/058059
§ 371 (c)(1),
(2) Date: Mar. 11, 2020

(87) PCT Pub. No.: WO2019/082023
PCT Pub. Date: May 2, 2019

(65) Prior Publication Data
US 2020/0270484 A1 Aug. 27, 2020

Related U.S. Application Data

(60) Provisional application No. 62/577,369, filed on Oct. 26, 2017.

(51) Int. Cl.
| | |
|---|---|
| *C09J 183/10* | (2006.01) |
| *C09J 7/30* | (2018.01) |
| *C08G 77/452* | (2006.01) |
| *C08G 77/00* | (2006.01) |
| *C08K 5/1545* | (2006.01) |

(52) U.S. Cl.
CPC .......... *C09J 183/10* (2013.01); *C08G 77/452* (2013.01); *C09J 7/30* (2018.01); *C08G 77/70* (2013.01); *C08K 5/1545* (2013.01); *C09J 2401/00* (2013.01); *C09J 2483/00* (2013.01)

(58) Field of Classification Search
None
See application file for complete search history.

(56) References Cited

U.S. PATENT DOCUMENTS

| | | |
|---|---|---|
| 2,676,182 A | 4/1954 | Daudt |
| RE24,906 E | 12/1960 | Ulrich |
| 3,627,851 A | 12/1971 | Brady |
| 3,691,140 A | 9/1972 | Silver |
| 3,772,247 A | 11/1973 | Flannigan |
| 4,166,152 A | 8/1979 | Baker |
| 4,636,432 A | 1/1987 | Shibano |
| 4,656,218 A | 4/1987 | Kinoshita |
| 4,707,531 A | 11/1987 | Shirahata |
| 4,737,559 A | 4/1988 | Kellen |
| 4,774,310 A | 9/1988 | Butler |
| 4,900,474 A | 2/1990 | Terae |
| 4,935,484 A | 6/1990 | Wolfgruber |
| 5,028,679 A | 7/1991 | Terae |
| 5,045,569 A | 9/1991 | Delgado |
| 5,110,890 A | 5/1992 | Butler |
| 5,118,775 A | 6/1992 | Inomata |
| 5,214,119 A | 5/1993 | Leir |
| 5,236,997 A | 8/1993 | Fujiki |
| 5,248,739 A | 9/1993 | Schmidt |
| 5,262,558 A | 11/1993 | Kobayashi |
| 5,302,685 A | 4/1994 | Tsumura |
| 5,319,040 A | 6/1994 | Wengrovius |
| 5,461,134 A | 10/1995 | Leir |
| 5,512,650 A | 4/1996 | Leir |
| 5,602,221 A | 2/1997 | Bennett |

(Continued)

FOREIGN PATENT DOCUMENTS

| | | |
|---|---|---|
| CN | 104017372 | 9/2014 |
| CN | 105153819 | 12/2015 |

(Continued)

OTHER PUBLICATIONS

"Scattering To Structural Foams", Encyclopedia of Polymer Science and Engineering, 1989, vol. 15, pp. 265-271.
Drtina, "Highly Cross-Linked Azlactone Functional Supports of Tailorable Polarity", Macromolecules, 1996, vol. 29, No. 13, pp. 4486-4489.
Grunert, "Progress In the Development of Cellulose Reinforced Nanocomposites", 2000, pp. 1-2.
Haraguchi, "Compositional Effects on Mechanical Properties of Nanocomposite Hydrogels Composed of Poly(N,N-dimethylacrylamide) and Clay", Macromolecules, 2003, vol. 36, No. 15, pp. 5732-5741.
Planes, "Improvement of the Thermal and Optical Performances of Protective Polydimethylsiloxane Space Coatings with Cellulose Nanocrystal Additives", American Chemical Society, 2016, vol. 08, pp. 28030-28039.
Zhang, "Facilitating Anion Transport in Polyolefin-Based Anion Exchange Membranes via Bulky Side Chains", ACS Applied Materials & Interfaces, 2016, vol. 08, pp. 23321-23330.

(Continued)

*Primary Examiner* — Marc S Zimmer
(74) *Attorney, Agent, or Firm* — Adrian L. Pishko

(57) ABSTRACT

The present disclosure provides an adhesive composition including a silicone-based adhesive and cellulose nanocrystals dispersed in the silicone-based adhesive. The present disclosure also provides an article including a substrate and a layer of the adhesive composition adhered to the substrate. Further, the present disclosure provides a method of making an adhesive composition. The method comprises mixing cellulose nanocrystals in a silicone-based adhesive to disperse the cellulose nanocrystals. The present disclosure additionally provides a method of making an article including disposing a layer of the adhesive composition on a substrate. The presence of the cellulose nanocrystals advantageously increases the water uptake capacity of the silicone-based adhesive while maintaining acceptable adhesive performance.

16 Claims, 1 Drawing Sheet

(56) References Cited

U.S. PATENT DOCUMENTS

| | | |
|---|---|---|
| 6,569,521 B1 | 5/2003 | Sheridan |
| 7,501,184 B2 | 3/2009 | Leir |
| 8,063,166 B2 | 11/2011 | Sherman |
| 8,765,881 B2 | 7/2014 | Hays |
| 2012/0114905 A1 | 5/2012 | Engler |
| 2012/0328877 A1* | 12/2012 | Shiramizu ............ C08B 15/05 536/63 |
| 2014/0080940 A1 | 3/2014 | Lee |
| 2015/0367021 A1 | 12/2015 | Wibaux |

FOREIGN PATENT DOCUMENTS

| | | |
|---|---|---|
| CN | 106009698 | 10/2016 |
| CN | 106702815 | 5/2017 |
| CN | 108030954 | 5/2018 |
| EP | 3266472 | 1/2018 |
| JP | 0236234 | 2/1990 |
| JP | 2018070852 | 5/2018 |
| WO | WO 1989-012618 | 12/1989 |
| WO | WO 1996-034028 | 10/1996 |
| WO | WO 1996-034030 | 10/1996 |
| WO | WO 1996-035458 | 11/1996 |
| WO | WO 1997-040103 | 10/1997 |
| WO | WO 1998-017726 | 4/1998 |
| WO | WO 2014-088622 | 6/2014 |
| WO | WO 2016-036632 | 3/2016 |
| WO | WO 2017-136188 | 8/2017 |
| WO | WO 2017-223261 | 12/2017 |
| WO | WO 2018-007595 | 1/2018 |
| WO | WO 2018-118497 | 6/2018 |

OTHER PUBLICATIONS

International Search Report for PCT International Application No. PCT/IB2018/058059, dated Jan. 14, 2019, 4 pages.

* cited by examiner

US 11,466,187 B2

COMPOSITION CONTAINING A SILICONE-BASED ADHESIVE AND CELLULOSE NANOCRYSTALS, AND METHODS AND ARTICLES

CROSS REFERENCE TO RELATED APPLICATIONS

This application is a national stage filing under 35 U.S.C. 371 of PCT/IB2018/058059, filed Oct. 17, 2018, which claims the benefit of U.S. Application No. 62/577,369, filed Oct. 26, 2017, the disclosures of which are incorporated by reference in their entirety herein.

FIELD

The present disclosure relates to the field of silicone-based adhesive compositions.

SUMMARY

In a first aspect, an adhesive composition is provided. The adhesive composition comprises a silicone-based adhesive and cellulose nanocrystals dispersed in the silicone-based adhesive. In some embodiments, the silicone-based adhesive comprises a polydiorganosiloxane polymer, and in others a block copolymer.

In a second aspect, an article is provided. The article comprises a substrate and a layer of the adhesive composition according to the first aspect adhered to the substrate.

In a third aspect, a method of making an adhesive composition is provided. The method comprises mixing cellulose nanocrystals in a silicone-based adhesive to disperse the cellulose nanocrystals. In some favored embodiments, the cellulose nanocrystals are not surface modified.

In a fourth aspect, a method of making an article is provided. The method comprises disposing a layer of the adhesive composition according to the first aspect on a substrate. In some favored embodiments, the method further includes exposing the layer of the adhesive composition to actinic radiation, heat, or a combination thereof.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
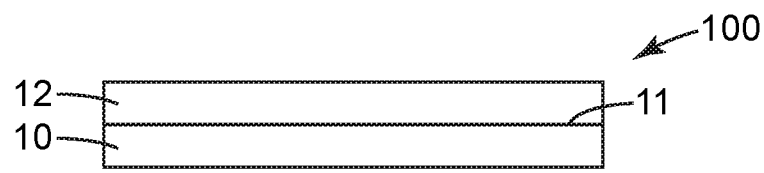
FIG. 1 is schematic cross-sectional view of an exemplary article according to the present disclosure.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION

The present disclosure concerns silicone-based adhesives containing cellulose nanocrystals to provide moisture absorption to the silicone-based adhesives.

In some uses of adhesive compositions (e.g., for medical dressings), there is a need to manage moisture that may be present at an adhesion site. Inclusion of a (e.g., hydrophilic) component in an adhesive composition can enhance the ability of the adhesive composition to adhere when moisture is present. Preferably, the component has a low level of extractability from the adhesive composition, and this is particularly advantageous in medical uses of the adhesive composition. It is also often desirable that the component not be readily extracted from the adhesive composition by the moisture (e.g., at a wound site).

Glossary

The term "dispersed" refers to one material distributed throughout another material. In some favored embodiments, the one material is essentially uniformly distributed throughout another material.

The term "hydrophilic" is used to describe materials that can be wet by water, or by aqueous solutions or suspensions (e.g., wound exudates).

The term "room temperature" refers to a temperature in the range of 20 to 25 degrees Celsius, inclusive.

The term "silicone-based" refers to a material (e.g., an adhesive) containing more than 50 wt. % silicone functional groups.

The terms "preferred", "preferably", and "favored" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "a", "an", and "the" are used interchangeably with "at least one" to mean one or more of the elements being described.

The term "and/or" means either or both. That is, the expression X and/or Y means X, Y or a combination thereof.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, 1-propenyl, and 1-butenyl.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, ethylhexyl, and octadecyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where (CO) denotes a carbonyl group and R is an alkyl group.

The term "aralkyl" refers to a monovalent group of formula —R—Ar where R is an alkylene and Ar is an aryl group. That is, the aralkyl is an alkyl substituted with an aryl. The term "substituted aralkyl" refers to an aralkyl substituted with one or more groups selected from halo, alkyl, haloalkyl, alkoxy, or alkoxycarbonyl. The aryl portion of the aralkyl is typically the group that is substituted.

The term "aralkylene" refers to a divalent group of formula —R—Ar— where R is an alkylene and Ar is an arylene (i.e., an alkylene is bonded to an arylene).

The term "aryl" refers to a monovalent group that is radical of an arene, which is a carbocyclic, aromatic compound. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, naphthyl, acenaphthyl, anthraquinonyl, phenanthryl, anthracenyl, pyrenyl, perylenyl, and fluorenyl. The term "substituted aryl" refers to an aryl substituted with one or more groups selected from halo, alkyl, haloalkyl, alkoxy, or alkoxycarbonyl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

Unless otherwise specified, "alkylene," "-alkylene-", "alkenylene", and "-alkenylene-" are the divalent forms of the "alkyl" and "alkenyl" groups defined above.

The term "carbonyl" refers to a divalent group of formula —(CO)— where the carbon atom is attached to the oxygen atom with a double bond. The term "carbonylamino" refers to a divalent group of formula —(CO)—NR$^2$— where R$^2$ is hydrogen, alkyl, aryl, aralkyl, or part of a heterocyclic group.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

Adhesive Compositions
Silicone-Based Adhesives

In a first aspect, an adhesive composition is provided. The adhesive composition comprises a silicone-based adhesive and cellulose nanocrystals dispersed in the silicone-based adhesive. Various silicone-based materials are suitable, including for instance random silicone polymers and block copolymers comprising silicone. In certain embodiments, silicone-based adhesives can comprise silicone gels (e.g., polydiorganosiloxanes), silicone polyurea block copolymers, polydiorganosiloxane polyoxamide block copolymers, or a combination thereof. If desired, one or more tackifiers may be added to the silicone-based adhesive.

Generally, silicone or silicone-based materials may be oils, fluids, gums, elastomers, or resins (e.g., friable solid resins). Generally, lower molecular weight, lower viscosity materials are referred to as fluids or oils, while higher molecular weight, higher viscosity materials are referred to as gums; however, there is no sharp distinction between these terms. Elastomers and resins have even higher molecular weights that gums, and typically do not flow. As used herein, the terms "fluid" and "oil" refer to materials having a dynamic viscosity at 25 degrees C. of no greater than 1,000,000 mPa·sec (e.g., less than 600,000 mPa·sec), while materials having a dynamic viscosity at 25 degrees C. of greater than 1,000,000 mPa·sec (e.g., at least 10,000,000 mPa·sec) are referred to as "gums".

Silicone gels are part of a class of materials typically known as filler-free silicone elastomers. Typical fillers that are absent from these materials are pyrogenic and precipitated silicas, silica aero-gels and carbon blacks. It is well known that covalent crosslinking of pure polysiloxanes yields elastomers whose mechanical strength is very low compared with that of organic elastomers. Silicone gels are typically understood to be crosslinked PDMS networks that exhibit greater extensibility, tack and a gelatinous consistency relative to crosslinked filler-free silicone elastomers. These physical properties result from the presence of free polysiloxane chains or polysiloxane chains that are covalently linked to the PDMS network only at one point. Crosslinked filler free silicone elastomers, or silicone gels, exhibit pronounced viscoelastic behavior. Silicone gels are highly dissipative under deformation, resulting in pronounced damping, self-healing and resiliency properties. Another key characteristic of silicone gels is a naturally tacky surface. This natural adhesion allows gels to gain a degree of physical adhesion to most common surfaces without the need for primers. Silicone gels retain much of the stress relief and self-healing qualities of a liquid while providing the dimensional stability of an elastomer. Silicone gels have been used to isolate circuits from the harmful effects of moisture and other contaminants and provide electrical insulation for high voltages. Additionally, silicone gels are used in healthcare applications, such as adhesive tapes and dressings, where very gentle removal from skin is desired. Silicone gels are softer than silicone pressure sensitive adhesives (PSAs), resulting in less discomfort when adhered to, and subsequently removed from, skin. The combination of moderate adhesive strength and tack make silicone gels suitable for many skin adhesive applications.

In certain embodiments, adhesive compositions of the present disclosure include a silicone gel that has a crosslinked poly(diorganosiloxane). The crosslinked poly(diorganosiloxane) has terminal end groups of Formula 1:

(1)

where R$^1$ is hydroxyl, alkyl, or aryl, and each R$^2$ is independently alkyl or aryl. The poly(diorganosiloxanes) have a poly(siloxane) backbone. In some embodiments, the poly(diorganosiloxane) can be a linear material described by Formula 2, illustrating a siloxane backbone with aliphatic and/or aromatic substituents:

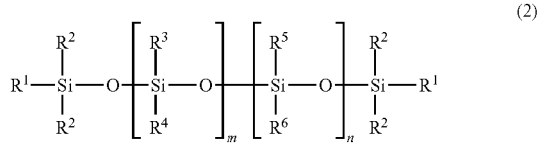

(2)

wherein each $R^1$ is independently hydroxyl, alkyl, or aryl, and wherein each $R^2$, $R^3$, $R^4$, $R^5$, and $R^6$ is independently alkyl or aryl, and m and n are integers, and at least one of m or n is not zero. An alkyl group can include 1 to about 20 carbon atoms, and an aryl group typically includes 6 to 10 carbon atoms. In some embodiments, one or more of the alkyl or aryl groups may contain a halogen substituent, e.g., fluorine. For example, in some embodiments, one or more of the alkyl groups may be —$CH_2CH_2C_4F_9$.

In some embodiments, $R^1$ and $R^2$ are methyl groups, i.e., the poly(diorganosiloxane) material is terminated by trimethylsiloxy groups. In some further embodiments, $R^3$ and $R^4$ are alkyl groups and n is zero, and the material is referred to as a poly(dialkylsiloxane). When the alkyl groups in a poly(dialkylsiloxane) are methyl groups, the material is a poly(dimethylsiloxane) ("PDMS"). The poly(diorganosiloxane) can be, for example, a PDMS having —Si(OH)(CH$_3$)$_2$ or —Si(CH$_3$)$_3$ terminal groups. In some embodiments, $R^3$ is an alkyl group, $R^4$ is an aryl group, and n is zero, i.e., the material is a poly(alkylarylsiloxane). In some embodiments, $R^3$ is methyl group and $R^4$ is a phenyl group, i.e., the material is poly(methylphenylsiloxane). In some embodiments, $R^3$ and $R^4$ are alkyl groups and $R^5$ and $R^6$ are aryl groups, i.e., the material is a poly(dialkyldiarylsiloxane). In some embodiments, $R^3$ and $R^4$ are methyl groups, and $R^5$ and $R^6$ are phenyl groups, i.e., the material is poly(dimethyldiphenylsiloxane).

In some embodiments, the poly(diorganosiloxane) materials can be a branched material described by Formula 3, illustrating a siloxane backbone that includes at least one linear or branched siloxane substituent among substituents $R^7$, $R^8$, $R^9$, and $R^{10}$:

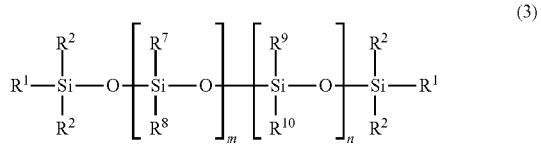

(3)

wherein each $R^1$ is independently hydroxyl, alkyl, or aryl, each $R^2$ is independently alkyl or aryl, and at least one of $R^7$, $R^8$, $R^9$, and $R^{10}$ is a linear or branched siloxane with alkyl or aryl (optionally including halogenated alkyl or aryl) substituents, the linear or branched siloxane having the terminal end group of Formula 1, and m and n are integers, and at least one of m or n is not zero. Any remaining R-groups among $R^7$, $R^8$, $R^9$, and $R^{10}$ in Formula 3 (i.e., if not a linear or branched siloxane) are independently alkyl or aryl (optionally including halogenated alkyl or aryl). Alkyl and aryl for Formula 3 are as defined for Formula 2.

As used herein, "nonfunctional groups" are either alkyl or aryl groups consisting of carbon, hydrogen, and in some embodiments, halogen (e.g., fluorine) atoms. As used herein, a "nonfunctionalized poly(diorganosiloxane) material" is one in which the $R^2$, $R^3$, $R^4$, $R^5$, $R^6$, $R^7$, $R^8$, $R^9$, and $R^{10}$ groups are nonfunctional groups.

Generally, crosslinked poly(diorganosiloxane) materials of the present disclosure can be formed from either silanol-terminated or non-functional poly(diorganosiloxane) materials. These silicone gel adhesives have excellent wetting characteristics, due to the very low glass transition temperature ($T_g$) and modulus of the crosslinked poly(diorganosiloxane) network. Rheologically, these gels exhibit similar storage moduli at bond making and bond breaking time scales, resulting in relatively low to moderate forces being required to debond the adhesive by peeling. This results in minimal to no skin trauma upon removal. Additionally, the elastic nature of the crosslinked gel prevents flow of the adhesive around hair during skin wear, further reducing the instances of pain during removal.

Suitable examples of poly(diorganosiloxane) materials useful for preparation of adhesive compositions of the present disclosure are commercially available, including a trimethylsilyl-terminated poly(dimethylsiloxane) silicone fluid available under the trade designation "AK 60000" from Wacker Chemical Corp. (Adrian, Mich.), a two-part soft skin adhesive available under the trade designation "DOW CORNING MG 7-9900" from Dow Corning (Midland, Mich.), and a poly(diorganosiloxane) fluid with silanol end groups available under the trade designation "OHX-4070" from Xiameter (Midland, Mich.).

Useful silicone-based (e.g., pressure sensitive) adhesive compositions include a MQ tackifying resin and a silicone polymer. The MQ tackifying resin and the silicone polymer can be present in the form of, e.g., a blend of MQ tackifying resin and silicone polymer, a reaction product of MQ tackifying resin and silicone polymer, e.g., a condensation cure or addition cure type reaction product, or a mixture thereof. Preferably the silicone polymer is present in a silicone-based pressure sensitive adhesive composition in an amount of from about 30 wt. % to about 70 wt. %, more preferably 35 wt. % to 65 wt %. The MQ tackifying resin is present in a silicone-based pressure sensitive adhesive composition in an amount of from about 30 wt. % to about 70 wt. %, preferably from about 40 wt. % to about 60 wt. %, more preferably 45 wt. % to 55 wt %.

Useful MQ tackifying resins include, for instance, MQ silicone resins, MQD silicone resins, and MQT silicone resins, which also may be referred to as copolymeric silicone resins and which preferably have a number average molecular weight of about 100 to about 50,000, more preferably about 500 to about 20,000 and generally have methyl substituents. The MQ silicone resins include both non-functional and functional resins, the functional resins having one or more functionalities including, for example, silicon-bonded hydrogen, silicon-bonded alkenyl, and silanol.

MQ silicone resins are copolymeric silicone resins having $R'_3SiO_{1/2}$ units (M units) and $SiO_{4/2}$ units (Q units). Such resins are described in, for example, Encyclopedia of Polymer Science and Engineering, vol. 15, John Wiley & Sons, New York, (1989), pp. 265 to 270, and U.S. Pat. Nos. 2,676,182; 3,627,851; 3,772,247; and 5,248,739, and incorporated herein by reference. MQ silicone resins having functional groups are described in U.S. Pat. No. 4,774,310, which describes silyl hydride groups, U.S. Pat. No. 5,262,558, which describes vinyl and trifluoropropyl groups, and U.S. Pat. No. 4,707,531, which describes silyl hydride and vinyl groups, each of which is incorporated herein by reference. The above-described resins are generally prepared in solvent. Dried or solventless MQ silicone resins are prepared as described in U.S. Pat. Nos. 5,319,040; 5,302,685; and 4,935,484, and incorporated herein by reference.

MQD silicone resins are terpolymers having $R'_3SiO_{1/2}$ units (M units), $SiO_{4/2}$ units (Q units), and $R'_2SiO_{2/2}$ units (D units) as described, e.g., in U.S. Pat. No. 5,110,890 and Japanese Kokai HEI 2-36234, and incorporated herein by reference.

MQT silicone resins are terpolymers having $R_3SiO_{112}$ units (M units), $SiO_{4/2}$ units (Q units), and $RSiO_{3/2}$ units (T units) (MQT resins).

Commercially available MQ resins include SR-545 MQ resin in toluene available from General Electric Co., Silicone Resins Division (Waterford, N.Y.), and MQOH resins which are MQ silicone resins in toluene available from PCR, Inc. (Gainesville, Fla.). Such resins are generally supplied in organic solvent. These organic solutions of MQ silicone resin may be used as is or may be dried by any number of techniques known in the art including, e.g., spray drying, oven drying, and steam separation, to provide a MQ silicone resin at 100 percent non-volatile content. The MQ silicone resin can also include blends of two or more silicone resins.

One example of a useful class of silicone polymers is silicone polyurea block copolymers. Silicone polyurea block copolymers include the reaction product of a polydiorganosiloxane diamine (also referred to as silicone diamine), a diisocyanate, and optionally an organic polyamine. Suitable silicone polyurea block copolymers are represented by the repeating unit of Formula 4:

ylene, 3,5,5-trimethyl-3-methylenecyclohexylene, 1,6-hexamethylene, 1,4-cyclohexylene, 2,2,4-trimethylhexylene and mixtures thereof; each Y is a polyvalent radical that independently is an alkylene radical of 1 to 10 carbon atoms, an aralkylene radical or an arylene radical preferably having 6 to 20 carbon atoms; each D is selected from the group consisting of hydrogen, an alkyl radical of 1 to 10 carbon atoms, phenyl, and a radical that completes a ring structure including B or Y to form a heterocycle; where B is a polyvalent radical selected from the group consisting of alkylene, aralkylene, cycloalkylene, phenylene, polyalkylene oxide, including for example, polyethylene oxide, polypropylene oxide, polytetramethylene oxide, and copolymers and mixtures thereof; m is a number that is 0 to about 1000; n is a number that is at least 1; and p is a number that is at least 10, preferably about 15 to about 2000, more preferably 30 to 1500.

Useful silicone polyurea block copolymers are described in, for instance, U.S. Pat. Nos. 5,512,650, 5,214,119, 5,461,134, 6,569,521; WO 96/35458, WO 98/17726, WO 96/34028, WO 96/34030 and WO 97/40103, and incorporated herein by reference.

One example of a useful class of silicone polymers is polydiorganosiloxane polyoxamide copolymers. Polydiorganosiloxane polyoxamide copolymers have both hard segments and soft segments. The soft segments are contributed by the silicone-based amines that have a polydiorganosiloxane segment. In many embodiments, the only soft segments in the copolymer are the polydiorganosiloxane seg-

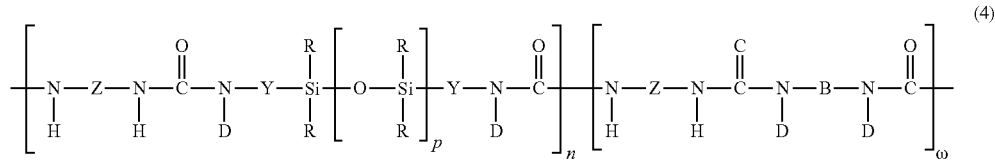

wherein each R is a moiety that, independently, is an alkyl moiety, preferably having about 1 to 12 carbon atoms, and may be substituted with, for example, trifluoroalkyl or vinyl groups, a vinyl radical or higher alkenyl radical preferably represented by the formula $R^2$ $(CH_2)_a CH=CH_2$ wherein $R^2$ is $-(CH_2)_b-$ or $-(CH_2)_c CH=CH-$ and a is 1, 2 or 3; b is 0, 3 or 6; and c is 3, 4 or 5, a cycloalkyl moiety having from about 6 to 12 carbon atoms and may be substituted with alkyl, fluoroalkyl, and vinyl groups, or an aryl moiety preferably having from about 6 to 20 carbon atoms and may be substituted with, for example, alkyl, cycloalkyl, fluoroalkyl arid vinyl groups or R is a perfluoroalkyl group as described in U.S. Pat. No. 5,028,679, and incorporated herein, or a fluorine-containing group, as described in U.S. Pat. No. 5,236,997 and incorporated herein, or a perfluoroether-containing group, as described in U.S. Pat. Nos. 4,900,474 and 5,118,775 and incorporated herein; preferably at least 50% of the R moieties are methyl radicals with the balance being monovalent alkyl or substituted alkyl radicals having from 1 to 12 carbon atoms, alkenylene radicals, phenyl radicals, or substituted phenyl radicals; each Z is a polyvalent radical that is an arylene radical or an aralkylene radical preferably having from about 6 to 20 carbon atoms, an alkylene or cycloalkylene radical preferably having from about 6 to 20 carbon atoms, preferably Z is 2,6-tolylene, 4,4'-methylenediphenylene, 3,3'-dimethoxy-4,4'-biphenylene, tetramethyl-m-xylylene, 4,4'-methylenedicyclohexments. The hard segments are contributed by the oxaylyamido-containing compound and include the Q group.

In certain embodiments, suitable polydiorganosiloxane polyoxamide copolymers comprise the following Formula 5:

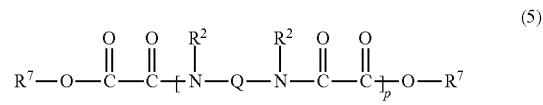

In this formula, each $R^7$ is phenyl or a fluorinated alkyl with an alpha-carbon that is non-fluorinated. Each $R^2$ is independently hydrogen, alkyl, aralkyl, aryl, or part of a heterocyclic group that includes Q and the nitrogen to which $R^2$ is attached. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. The variable p is an integer equal to at least 1. Group $R^7$ is a phenyl or a fluorinated alkyl with an alpha-carbon that is non-fluorinated. The fluorinated alkyl can be linear or branched and often contains 2 to 10 carbon atoms, 2 to 6 carbon atoms, or 2 to 4 carbon atoms. Examples of $R^7$ include, but are not limited to, —$CH_2CF_3$, —$CH_2CHF_2$, —$CH_2CH_2F$, —$CH(CF_3)_2$, and —$CH_2CH_2CH_2F$. Methods for making the polydiorganosiloxane polyoxamide copolymers of Formula 5 can be found in U.S. Pat. No. 8,765,881, incorporated herein by reference. Additional suitable polydiorganosiloxane polyoxamide copolymers and methods of making them can be found in U.S. Pat. Nos. 7,501,184 and 8,063,166, incorporated herein by reference.

Adhesive compositions of the present disclosure include cellulose nanocrystals distributed (e.g., dispersed) in the silicone-based adhesive. The cellulose nanocrystals can absorb moisture (e.g., water, wound exudates, etc.). In some instances, an adhesive composition of the present disclosure can absorb water in amount (by weight) that is at least 20% of an initial weight of the (hydrophobic) adhesive composition (see Examples section).

Cellulose Nanocrystals

"Primary particle size" refers to the mean diameter of a single (non-aggregate, non-agglomerate) particle. There are various methods for production of these secondary particles, giving granules with varying morphology and varying properties. In some embodiments, the secondary particles may be referred to as "agglomerates". An "agglomerate" refers to a weak association between primary particles which may be held together by charge or polarity and can be broken down into smaller entities. These weakly bound agglomerates would typically break down during high energy mixing processes. In some embodiments, the agglomerate my further comprise organic or inorganic binder.

Cellulose nanocrystals are typically extracted as a colloidal suspension by acid hydrolysis of typically chemical wood pulps, but other cellulosic materials, such as bacteria, cellulose-containing sea animals (e.g. tunicate), or cotton can be used. Cellulose nanocrystals are constituted of cellulose, a linear polymer of beta (1 to 4) linked D-glucose units, the chains of which arrange themselves to form crystalline and amorphous domains.

Cellulose nanocrystals have a unique combination of characteristics such as high axial stiffness, high tensile strength, low coefficient of thermal expansion, thermal stability up to about 300° C., high aspect ratio, low density, lyotropic liquid crystalline behavior, and shear thinning rheology in cellulose nanocrystal suspensions. Additionally, cellulose nanocrystals are renewable, sustainable, and carbon neutral, like the sources from which they are extracted.

The physical dimensions of cellulose nanocrystals can vary depending on the raw material used in the extraction. In one embodiment, the cellulose nanocrystal has an average primary particle size (maximum dimension of a cross-section of the cellulose nanocrystal, perpendicular to the length) of at least 2, 4, or even 5 nanometers (nm) and at most 10, 20, 30, or even 50 nm; and an average length (maximum dimension of the cellulose nanocrystal) of at least 50, 75, or even 100 nm and at most 150, 200, 250, 500, 750, or even 1000 nm (e.g., 1 micrometer). The cross-sectional morphology of the nanocrystals is typically rounded, but can be rectangular, or square. Typically, the cellulose nanocrystals have a high aspect ratio (ratio of height versus length). In one embodiment, the cellulose nanocrystals have an aspect ratio of 10 to 100. The cellulose nanocrystals can exist as agglomerate prior to being dispersed (e.g., in an adhesive or in water). The dimensions of the cellulose nanocrystals may be determined based on transmission electron microscopy (TEM), scanning electron microscopy (SEM), atomic force microscopy, or by other suitable means. Typically, the morphology is determined on dried samples.

Cellulose nanocrystals can also be characterized by high crystallinity (e.g., at least 60%, 70%, 80%, 85%, or even 90%) approaching the theoretical limit of the cellulose chains. Hydrogen bonding between cellulose chains can stabilize the local structure in cellulose nanocrystals, and plays a key role in the formation of crystalline domains. Crystallinity, defined as the crystalline fraction of the sample can influence the physical and chemical behavior of cellulose nanocrystals.

The surfaces of the cellulose nanocrystals typically comprise a plurality of functional groups, including hydroxyl and sulfate half-ester groups. In a typical embodiment, the surface of the cellulose nanocrystals are not modified. Advantageously, such a typical embodiment avoids the process step(s) involved in modifying the cellulose nanocrystal surface with functional groups.

Previously, cellulose nanocrystals have been surface modified to prevent self-aggregation when combined with a hydrophobic matrix (see, e.g., ACS Appl. Mater. Interfaces, 2016, vol. 8, p. 28031). It has been discovered that adhesive compositions according to at least certain embodiments of the present disclosure can be prepared of non-surface modified cellulose nanocrystals dispersed in a silicone-based adhesive without extensive self-aggregation of the unmodified cellulose nanocrystals. In alternate embodiments, functional groups (e.g., hydroxyl and sulfate half-ester groups) on the surfaces of the cellulose nanocrystals can optionally be modified, such as by acylation or silylation.

The density of the cellulose nanocrystals is typically less than 1.6, 1.4, 1.2, or even 1.1 g/cm$^3$ at ambient conditions.

The zeta potential measures the potential difference existing between the surface of a solid particle immersed in a conducting liquid (e.g. water) and the bulk of the liquid of the cellulose nanocrystal surface. The cellulose nanocrystals have a zeta potential higher (i.e., less negative) than −50, −45, −40, −35, −30, or even −25 mV based on dynamic light scattering.

The cellulose nanocrystals typically provide a pH of less than 7.5, 7.0, 6.5, or even 6.0 and greater than 4.5, 5.0, or even 5.5 when dispersed in deionized water and measured at ambient conditions.

Based on the processing to form the cellulose nanocrystals, residual sulfur may be present. In one embodiment, the cellulose nanocrystals comprise greater than 0.01% and less than 1, 0.8, 0.5, 0.1 or even 0.05% sulfur content. An exemplary method to determine sulfur content is inductively coupled plasma.

Cellulose nanocrystals may be obtained, for example, from CelluForce, Montreal, Canada; Melodea Ltd., Israel; American Process Inc., Atlanta, Ga.; Blue Goose Biorefineries Inc., Saskatoon, Canada; and the USDA Forest Products Laboratory, Madison, Wis. via the University of Maine.

Methods of Making Adhesive Compositions

In another aspect of the present disclosure, a method of making an adhesive composition is provided. The method comprises mixing cellulose nanocrystals in a silicone-based adhesive to disperse the cellulose nanocrystals. In typical embodiments, the cellulose nanocrystals are provided as dry powders. A dry powder is then combined with a silicone-based adhesive at the concentrations described below. Suitable mixers include planetary mixers and ribbon-paddle blends, such as available from Ross; as well as various bladeless mixers including TURBULA™ Shaker-Mixers and dyna-MIX™ 3-dimensional rotational mixers available from Glen Mills Inc. (Clifton, N.J.), and SpeedMixers™, available from Flack Tek (Landrum, S.C.). Without intending to be bound by theory, although agglomerates of cellulose nanocrystals are typically broken up during dispersion of the cellulose nanocrystals in the silicone-based adhesive, the primary particle size of the cellulose nanocrystals is substantially the same prior to and after combining with the silicone-based adhesive. Often, a visual (e.g., optical) check can determine sufficient dispersion of the cellulose nanocrystals without necessarily requiring an analytical measurement to verify the extent of dispersion of the cellulose nanocrystals.

In certain embodiments, the cellulose nanocrystals are present in an adhesive composition in an amount of 0.5 weight percent (wt. %) or more of the total adhesive composition, 1 wt. % or more, 2 wt. % or more, 3 wt. % or more, 4 wt. % or more, 5 wt. % or more, 6 wt. % or more, 8 wt. % or more, 10 wt. % or more, 12 wt. % or more, or 14 wt. % or more of the total adhesive composition; and 20 wt. % or less of the total adhesive composition, 19 wt. % or less, 18 wt. % or less, 17 wt. % or less, 16 wt. % or less, 15 wt. % or less, 13 wt. % or less, 11 wt. % or less, or even 9 wt. % or less of the total adhesive composition. Stated another way, the cellulose nanocrystals may be present in an amount of 0.5 to 20 weight percent, 0.5 to 9 weight percent, or 10 to 20 weight percent of the total adhesive composition.

The adhesive composition may optionally further comprise additives including antimicrobial agents, (e.g. silane-treated or untreated) fillers, anti-sag additives, thixotropes, processing aids, waxes, and UV stabilizers.

Cellulose nanocrystals typically include approximately 2-3 wt. % bound water, which can be driven off by heat, such as in an oven. In high humidity conditions, cellulose nanocrystals have been known to comprise up to about 8 wt. % bound water. It was unexpectedly discovered, however, that when dispersed in a hydrophobic adhesive (e.g., a silicone-based adhesive), even a small loading of cellulose nanocrystals can provide an increase in water uptake of the adhesive composition. For instance, a percent Swell Test (e.g., % Swell) can be performed to evaluate the percent swell of an adhesive composition (as further described in the examples). The % swell of adhesive compositions according to at least certain embodiments of the disclosure comprises 4% or greater, 5% or greater, 7% or greater, 10% or greater, 12% or greater, 15% or greater, 17% or greater, 20% or greater, 22% or greater, 25% or greater, 27% or greater, 30% or greater, 32% or greater, 35% or greater, 37% or greater, or even 40% or greater, as determined by the Swell Test. In certain embodiments, the presence of cellulose nanocrystals in an adhesive composition provides an increase in percent swell over the same composition not containing the (e.g., dispersed) cellulose nanocrystals of 1% or greater, 2% or greater, 3% or greater, 4% or greater, 5% or greater, 6% or greater, 7% or greater, 10% or greater, 12% or greater, 15% or greater, 17% or greater, 20% or greater, 22% or greater, or even 25% or greater, as determined by the Swell Test.

Advantageously, the incorporation of cellulose nanocrystals into a silicone-based adhesive has a minimal to no measurable negative effect on one or more properties of the adhesive composition selected from wet peel adhesion strength, dry peel adhesion strength, and shear adhesion strength to polypropylene or stainless steel. For instance, in certain embodiments, the adhesive composition exhibits a wet peel adhesion on stainless steel that is no less than 70%, 75%, 80%, 85%, or 90% of the wet peel adhesion of the same composition without the cellulose nanocrystals, as determined by a Wet Peel Adhesion Strength Test (as described in the examples). Similarly, in certain embodiments, the adhesive composition exhibits a dry peel adhesion on stainless steel that is no less than 70%, 75%, 80%, 85%, or 90% of the dry peel adhesion of the same composition without the cellulose nanocrystals, as determined by a Dry Peel Adhesion Strength Test (as described in the examples). In certain embodiments, the adhesive composition exhibits a room temperature shear of greater than 10,000 minutes or of no less than 90% of the room temperature shear of the same composition without the cellulose nanocrystals, as determined by a Shear Adhesion Strength Test—Polypropylene (Method A) or by a Shear Adhesion Strength Test—Polypropylene (Method B) (each as described in the examples) at room temperature. Moreover, in certain embodiments, the adhesive composition exhibits a room temperature shear of greater than 10,000 minutes or of no less than 90% of the room temperature shear of the same composition without the cellulose nanocrystals, as determined by a Shear Adhesion Strength Test—Stainless Steel (as described in the examples) at room temperature.

Moreover, the cellulose nanocrystals incorporated in a silicone-based adhesive advantageously are not readily extractable from the silicone-based adhesive using water. For example, in at least certain embodiments of the adhesive compositions of the present disclosure, less than 5 wt. %, less than 3 wt. %, less than 2 wt. %, less than 1 wt. %, or even less than 0.5 wt. % of the cellulose nanocrystals in the silicone-based adhesive are extractable from the silicone-based adhesive, as determined by a % Extractables Test (as described in the examples). Accordingly, the integrity of the adhesive composition is generally maintained upon water absorption.

Articles

In a second aspect, an article is provided. The article comprises a substrate and a layer of the adhesive composition according to the first aspect (described in detail above) adhered to the substrate. Referring to FIG. 1, a schematic cross-sectional view is provided of an exemplary article 100 comprising a substrate 10 having a first major surface 11 and a layer of an adhesive composition 12 disposed on (e.g., adhered to) the first major surface 11 of the substrate 10. The layer of the adhesive composition 12 covers at least a portion of the first major surface 11 of the substrate 10.

The thickness of the layer of adhesive composition is not particularly limited, and can comprise a thickness of 15 micrometers (µm) or greater, 20 µm or greater, 25 µm or greater, 30 µm or greater, 50 µm or greater, 75 µm or greater, 100 µm or greater, 125 µm or greater, or even 150 µm or greater; and 300 µm or less, 275 µm or less, 250 µm or less, 225 µm or less, 200 µm or less, or even 175 µm or less.

Figure 2:
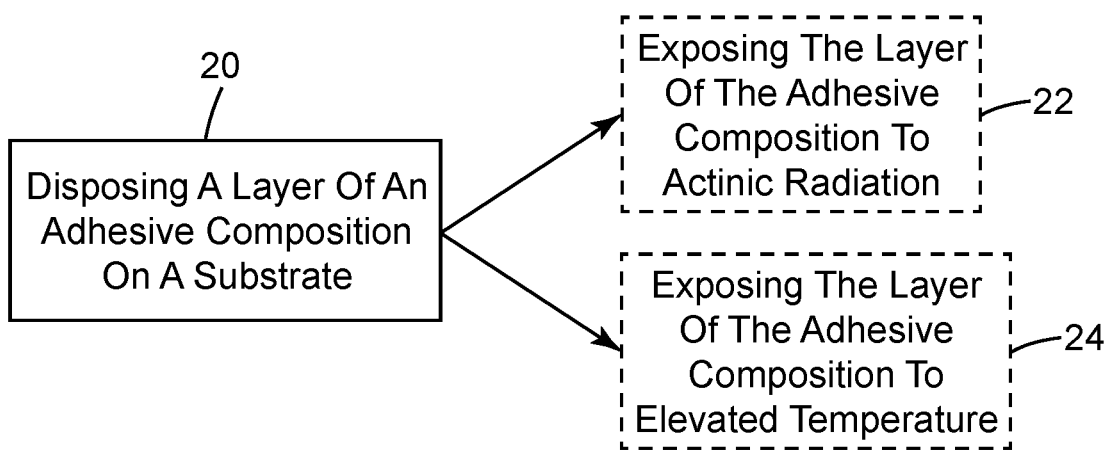
FIG. 2 is a flow chart of an exemplary method of making an article according to the present disclosure.

The article is typically an adhesive article, suitable for adhering at least one substrate to another substrate or material (e.g., skin). The substrate of the article is not limited, and can comprise for instance and without limitation, paper, polymeric film, metal, fiber reinforced polymeric material, woven cloth (e.g., fabric, gauze, etc.), non-woven matrix (e.g., felt, sponge, gauze, etc.), or a combination thereof Methods of Making Articles In a fourth aspect, a method of making an article is provided. The method comprises disposing a layer of the adhesive composition according to the first aspect on a substrate. In some favored embodiments, the method further includes exposing the layer of the adhesive composition to actinic radiation, heat, or a combination thereof. Referring to FIG. 2, a flow chart is provided comprising disposing a layer of an adhesive composition on a substrate 20, and optionally exposing the layer of the adhesive composition to actinic radiation 22 or optionally exposing the layer of the adhesive composition to an elevated temperature 24. Actinic radiation includes i.e., radiation that leads to the production of photochemical activity. For example, actinic radiation may comprise electron beam (e-beam) radiation or radiation of from about 250 to about 700 nm. Sources of actinic radiation include e-beam units, tungsten halogen lamps, xenon and mercury arc lamps, incandescent lamps, germicidal lamps, fluorescent lamps, lasers and light emitting diodes. UV-radiation can be supplied using a high intensity continuously emitting system such as those available from Fusion UV Systems. E-beam radiation can be supplied using an ELECTROCURTAIN CB-300 e-beam unit (Energy Sciences Incorporated, Wilmington, Mass.). Typically, e-beam irradiation will be carried out with an acceleration voltage of between 100 and 300 keV and a dose of 2 to 9 MRad. In some embodiments, the adhesive composition is exposed to an elevated temperature (e.g., heat). Application of suitable elevated temperature typically comprises subjecting the article to heat in an oven set at a temperature of 60 to 200 degrees Celsius. Exposure of the layer of the adhesive composition to actinic radiation or heat can result in at least partial crosslinking of the silicone-based adhesive.

Select Embodiments of the Disclosure

Embodiment 1 is an adhesive composition. The adhesive composition comprises a silicone-based adhesive and cellulose nanocrystals dispersed in the silicone-based adhesive.

Embodiment 2 is the adhesive composition of embodiment 1, wherein the silicone-based adhesive comprises a random polymer.

Embodiment 3 is the adhesive composition of embodiment 1, wherein the silicone-based adhesive comprises a block copolymer.

Embodiment 4 is the adhesive composition of any of embodiments 1 to 3, wherein the silicone-based adhesive comprises a polydiorganosiloxane.

Embodiment 5 is the adhesive composition of any of embodiments 1 or 3, wherein the silicone-based adhesive comprises a silicone polyurea block copolymer, a polydiorganosiloxane polyoxamide block copolymer, or a combination thereof.

Embodiment 6 is the adhesive composition of any of embodiments 1 to 5, wherein the silicone-based adhesive comprises polydimethylsiloxane.

Embodiment 7 is the adhesive composition of any of embodiments 1 to 6, wherein the silicone-based adhesive further comprises a tackifier.

Embodiment 8 is the adhesive composition of any of embodiments 1 to 7, wherein the cellulose nanocrystals are present in an amount of 0.5 to 20 weight percent, 0.5 to 9 weight percent, or 10 to 20 weight percent of the total adhesive composition.

Embodiment 9 is the adhesive composition of any of embodiments 1 to 8, wherein the cellulose nanocrystals have a maximum primary particle size of less than 1 micrometer.

Embodiment 10 is the adhesive composition of any of embodiments 1 to 9, wherein the cellulose nanocrystals are not surface modified.

Embodiment 11 is the adhesive composition of any of embodiments 1 to 10, wherein the adhesive composition exhibits a wet peel adhesion on stainless steel that is no less than 70%, 80%, or 90% of the wet peel adhesion of the same composition without the cellulose nanocrystals, as determined by a Wet Peel Adhesion Strength Test.

Embodiment 12 is the adhesive composition of any of embodiments 1 to 11, wherein the adhesive composition exhibits a dry peel adhesion on stainless steel that is no less than 70%, 80%, or 90% of the dry peel adhesion of the same composition without the cellulose nanocrystals, as determined by a Dry Peel Adhesion Strength Test.

Embodiment 13 is the adhesive composition of any of embodiments 1 to 12, wherein the adhesive composition exhibits a room temperature shear of greater than 10,000 minutes or of no less than 90% of the room temperature shear of the same composition without the cellulose nanocrystals, as determined by a Shear Adhesion Strength Test—Polypropylene (Method A) or a Shear Adhesion Strength Test—Polypropylene (Method B) at room temperature.

Embodiment 14 is the adhesive composition of any of embodiments 1 to 13, wherein the adhesive composition exhibits a room temperature shear of greater than 10,000 minutes or of no less than 90% of the room temperature shear of the same composition without the cellulose nanocrystals, as determined by a Shear Adhesion Strength Test—Stainless Steel at room temperature.

Embodiment 15 is the adhesive composition of any of embodiments 1 to 14, wherein the adhesive composition exhibits a swell of at least 4%, as determined by a Swell Test.

Embodiment 16 is the adhesive composition of any of embodiments 1 to 15, wherein less than 2 weight percent of the cellulose nanocrystals are extractable from the adhesive composition, as determined by a % Extractables Test.

Embodiment 17 is an article. The article comprises a substrate and a layer of the adhesive composition according to any of embodiments 1 to 16 adhered to the substrate.

Embodiment 18 is the article of embodiment 17, wherein the layer of adhesive composition has a thickness of 20 micrometers to 300 micrometers.

Embodiment 19 is the article of embodiment 17 or embodiment 18, wherein the substrate comprises at least one of paper, polymeric film, metal, fiber reinforced polymeric material, woven cloth, and non-woven matrix.

Embodiment 20 is a method of making an adhesive composition. The method comprises mixing cellulose nanocrystals in a silicone-based adhesive to disperse the cellulose nanocrystals.

Embodiment 21 is the method of embodiment 20, wherein the adhesive composition exhibits a swell of at least 4% percent, as determined by a Swell Test.

Embodiment 22 is a method of making an article. The method comprises disposing a layer of the adhesive composition of any of embodiments 1 to 16 on a substrate.

Embodiment 23 is the method of embodiment 22, further comprising exposing the layer of the adhesive composition to actinic radiation.

Embodiment 24 is the method of embodiment 23, wherein the actinic radiation comprises e-beam radiation.

Embodiment 25 is the method of embodiment 22, further including exposing the article to an elevated temperature.

EXAMPLES

Objects and advantages of this disclosure are further illustrated by the following examples, but the particular materials and amounts thereof recited in these examples, as well as other conditions and details, should not be construed to unduly limit this disclosure.

Materials

| Designation | Description |
| --- | --- |
| Cellulose nanocrystals (CNC) | A solid white powder of cellulose nanocrystalline (CNC) particles which have a maximum dimension of 50 micrometers, as received, 150 nanometers once dispersed in water, a pH in water of 6-7, and an ionic strength of 230-270 millimoles/kilogram, made by CelluForce, Montreal, Quebec, Canada. |

| Designation | Description |
| --- | --- |
| OHX-4070 | A 100% silicone fluid polymer fluid having a viscosity of 50,000 centiPoise and a silanol content of 0.04%, believed to be a polydimethylsiloxane fluid, which can be used as an intermediate for silicone-based sealant manufacturing, available under the trade designation XIAMETER OHX-4070 POLYMER from Dow Corning Midland, MI. |
| 803TF | A white powder which is the co-hydrolysis product of tetraalkoxy silane (Q unit) and trimethyl-ethoxy silane (M unit) the chemical structure of which can be seen as a three dimensional network of polysilicic acid units which are endblocked with trimethylsilyl groups, having some residual ethoxy and hydroxy functions present, with ratio of M to Q units of approximately 0.67, an average particle size of approximately 10 micrometers, a hydroxyl content of no more than 0.30%, and which functions as a tackifer resin when used in silicone adhesive compositions, available under the trade designation WACKER MQ 803 TF SILICONE RESIN POWDER from Wacker Chemical Corporation, Adrian, MI. |
| BIO-PSA | An amine-compatible silicone adhesive solution produced through a condensation reaction of a silanol endblocked polydimethyl-siloxane (PDMS) with a silicate resin after which residual silanol functionality is capped with trimethylsiloxy groups, the solution having a viscosity of 1200 centiPoise and 61.6% solids content in ethyl acetate, available under the trade designation BIO-PSA 7-4302 SILICONE ADHESIVE from Dow Corning Corporation, Midland, MI. |
| Backing Film 1 | A backing film was provided by extruding a thermoplastic polyester elastomer onto a nonwoven polyester material, wherein the elastomer material had a three second Shore D hardness of 32 as tested per ISO 868 and a melting temperature of approximately 212° C. The backing had a total thickness of 0.0047 inches (119 micrometers). |
| Backing Film 2 | A 0.002 inch (0.05 millimeter) thick polyester film having a primer treatment on one side, available under the trade designation HOSTAPHAN 3SAB from Mitsubishi Polyester Film, Incorporated, Greer, SC. |
| Release Film | A polyester film having a fluorosilicone treatment on one side and having a thickness of 0.002 inches (51 micrometers), available under the trade designation SILFLU 1R82001 from Siliconature USA LLC, Chicago, IL. |
| SR 545 | A 60 weight percent solids solution of MQ silicate resin in toluene, available under the trade designation SR-545 from GE Silicones, Waterford, NY. |

Test Methods

Thickness Measurements

The thickness of the pressure sensitive adhesive (PSA) layer of a tape sample was measured using a Digimatic Indicator (ID-110E Series Model 543-221-1, Mitutoyo American Corporation, Aurora, Ill.) equipped with an 8 millimeter flat tip. The indicator was first zeroed by placing only the backing film in the indicator. Next, thickness measurements were made in three different locations on the PSA tape sample. One or two tape samples were evaluated and the average of all the readings was reported.

% Swell

The % swell of silicone adhesive samples was determined as follows. Samples of the backing film and Tape (backing film coated with silicone adhesive) measuring 2.5 centimeters in diameter were die cut and, after removal of the Release Film (if present), were weighed and their masses were recorded. Each sample was placed in a wire-mesh basket, measuring 3.8 centimeters by 3.8 centimeters, and loosely covered with a wire-mesh square, measuring 3.18 centimeters by 3.18 centimeters, to prevent the samples from folding on themselves. The samples in the wire-mesh baskets were placed in a jar with 1.9 liters of approximately 23° C. deionized water overnight (approximately 16 to 18 hours) after which they were removed from the water bath. The wire-mesh square was taken off the sample and the sample was placed on a clean, dry lint-free tissue and gently blotted to remove surface moisture. Each sample was again weighed, and each mass was recorded. Three samples were run and the average % Swell value reported. % Swell was calculated as the percent increase in mass of the silicone adhesive from the initial mass of the silicone adhesive as shown below:

$B1$=initial mass of backing
$B2$=swelled mass of backing
$T1$=initial mass of tape
$T2$=swelled mass of tape
$W1=T1-B1$=initial mass of silicone adhesive
$W2=T2-B2$=swelled mass of silicone adhesive
% Swell=$[(W2-W1)/W1] \times 100\%$ % Extractables The extractables content was determined as follows. The final, weighed tape samples from the "% Swell" test method were placed into a pan and dried for 48 hours at 70° C. The dried samples were then weighed to obtain a mass of the dried tape sample. The change in mass of the dried tape sample from the mass of the initial tape sample was determined and a % Extractables calculated as follows:

T1=initial mass of tape sample
T3=dried mass of tape sample
% Extractables=[(T1−T3)/T1]×100

Dry Peel Adhesion Strength

Dry peel adhesion strength was measured at 74° F. (23° C.) and 50% relative humidity (RH) using an IMASS Model 2100 Slip/Peel Tester (Instrumentors Incorporated, Strongsville, Ohio) equipped with a 25 pound load cell. A tape test specimen measuring 0.5 inch (1.27 centimeters) wide by approximately 6 inches (15.2 centimeters) long was applied to a flat, rigid stainless steel (SS) or polypropylene (PP) substrate. Stainless steel substrates, 0.052 inches (1.31 millimeters) thick, were wiped once with methyl ethyl ketone (MEK) and a lint free tissue, then allowed to air dry prior to use. Polypropylene substrates, 0.19 inches (4.80 millimeters) thick, were wiped once with isopropyl alcohol (IPA) and a lint free tissue, then allowed to air dry prior to use. A 2.2 kilogram rubber roller was rolled back and forth four times over a 4 inch (10.16 centimeters) length of the test specimen to ensure intimate contact with the substrate surface. The free end of the tape test specimen was doubled back at an angle of 180° and attached to the load cell apparatus. The substrate was attached to the moveable platen on the instrument. The peel test was run at a constant rate of 12 inches/minutes (30.48 centimeters/minute) and the average peel force was recorded in ounces/0.5 inch and normalized to ounces/inch. Six test specimens were evaluated and the results used to obtain an average value in ounces/inch (Newtons/decimeter).

Wet Peel Adhesion Strength

Wet peel adhesion strength was determined in the same manner as described for the test method "Dry Peel Adhesion Strength" with the following modifications. Deionized water was dripped onto the cleaned substrate surface to provide a thickness of 3 millimeters over an area measuring 1 inch by 5 inches (25.4 millimeters by 127 millimeters). The tape test specimen was applied onto the water coated area and rolled down. This process was repeated for a second tape test specimen in an area adjacent to the first test specimen, with care taken not to wet the first applied specimen.

Shear Adhesion Strength—Stainless Steel

Shear adhesion strength on a stainless steel (SS) substrate was determined at 74° F. (23° C.) and 50% RH as follows. A tape test specimen measuring 1 inch (2.54 centimeters) width and approximately 5 inches (12.7 centimeters) long was adhered to a flat, rigid stainless steel substrate with 1 inch (2.54 centimeters) of length of the test specimen in contact with the substrate and the remaining length extended beyond the edge of the substrate. The substrate was wiped once with methyl ethyl ketone (MEK) and a lint free tissue, then allowed to air dry prior to use. A 2.2 kilogram rubber roller was rolled back and forth one time over the adhered portion. After equilibration at room temperature for 15 minutes the substrate with test specimen adhered thereto was placed in a hanging rack, at room temperature, that supported the substrate at an angle of 2 degrees from vertical. A 250 gram weight was hung from the free end of the adhered test specimen. The time (in minutes) at which the weight fell due to the test specimen releasing from the plate, was recorded. Three tape test specimens were evaluated and the average failure time obtained. This was reported as shear adhesion strength.

Shear Adhesion Strength—Polypropylene (Method A)

Shear adhesion strength on a polypropylene (PP) substrate was determined in the same manner as described for the test method "Shear Adhesion Strength—Stainless Steel" with the following modifications. A flat, rigid polypropylene substrate was used in place of the stainless steel substrate. A tape test specimen measuring 0.5 inch (1.27 centimeters) width and approximately 5 inches (12.7 centimeters) long was adhered to a flat, rigid polypropylene substrate with 1 inch (2.54 centimeters) of length of the test specimen in contact with the substrate and the remaining length extended beyond the edge of the substrate. If the test specimen did not fail by 10,000 minutes the result was recorded as "10,000+" and the 250 gram weight was replaced with a 500 gram weight. If the test specimen did not fail by 10,000 minutes with a 500 gram weight the result was recorded as "10,000+".

Shear Adhesion Strength—Polypropylene (Method B)

Shear adhesion strength on a polypropylene (PP) substrate was determined in the same manner as described for the test method "Shear Adhesion Strength—Stainless Steel—Method A" with the following modification. A 100 gram weight was hung from the free end of the adhered test specimen in place of the 250 gram weight. If the test specimen did not fail by 10,000 minutes the result was recorded as "10,000+".

Preparation of Polydiorganosiloxane-Polyoxamide Block Copolymer (SiOxCp) Adhesive The polydisiloxane polyoxamide elastomer used in the pressure sensitive adhesive compositions of the Examples below, and having a number average molecular weight of about 20,000 grams/mole (amine (nitrogen) equivalent weight of about 10,000 grams/mole), was like that described in Example 12 of U.S. Pat. No. 8,765,881. MQ resin tackifier resin, SR 545, was added in an amount to provide an elastomer:tackifier weight ratio of 1:1. The resulting mixture was diluted with ethyl acetate in a glass jar which was then tightly sealed and placed on a roller at about 2-6 rpm for at least 24 hours prior to coating. The resulting solution contained a calculated amount of 35 wt % solids.

Preparation of Silicone-Polyurea Block Copolymer (SPUCp) Adhesive

The silicone-polyurea block copolymer-based pressure-sensitive adhesive composition used in the Examples below was prepared according to the method described for Example 28 in U.S. Pat. No. 6,569,521, with the final pressure sensitive adhesive solution containing approximately 30 wt % solids and having a silicone-polyurea block copolymer:MQ tackifier resin (SR 545) weight ratio of 1:1.

Examples 1-3 and Comparative Example 1 (C1)

An Adhesive Precursor was provided by combining 345 grams of OHX-4070 and 155 grams of 803TF tackifier resin in a container and mixing by mechanical means. Compositions containing the materials and amounts shown in Table 1 were prepared by mixing the materials in a cup using a centrifugal resin mixer (MAX 100 mixing cup and a Model DAC 150.1 FVZ-K SPEEDMIXER, both available from FlackTec Incorporated, Landrum, S.C.) at 2000 rpm for one minute, then at 2400 rpm for one minute, and finally at 2000 rpm for three minutes to ensure a uniform dispersion was obtained. The CNC component was added as a solid powder.

TABLE 1

Compositions

| Example | Adhesive Precursor grams) | CNC (grams) | Adhesive Precursor (Weight %) | CNC (Weight %) |
|---|---|---|---|---|
| C1 | 60.0 | 0.0 | 100 | 0 |
| 1 | 57.6 | 2.4 | 96 | 4 |
| 2 | 54.0 | 6.0 | 90 | 10 |
| 3 | 48.0 | 12.0 | 80 | 20 |

The compositions shown in Table 1 were then coated onto the thermoplastic elastomer side of Backing Film 1 using a knife-over-bed coating station with a gap setting of 0.007 inches (178 micrometers) greater than the thickness of Backing Film 1. The coated Backing Film 1 was exposed on the coated side to e-beam irradiation using an ELECTROCURTAIN CB-300 e-beam unit (Energy Sciences Incorporated, Wilmington, Mass.) at an accelerating voltage of 280 Kiloelectron Volts (KeV) to provide a total dose of 6.7 MegaRads to provide pressure sensitive adhesive tape articles CNC (Weight %). The resulting tape articles were then covered with the Release Film and stored at 74° F. (23.3° C.) and 50% relative humidity (RH) for at least 24 hours before evaluation as described in the test methods. The results are shown below in Tables 3-5.

TABLE 2

Thickness Results

| Example | CNC (Weight %) | Thickness inches (micrometers) |
|---|---|---|
| C1 | 0 | 0.0046 (117) |
| 1 | 4 | 0.0049 (124) |
| 2 | 10 | 0.0049 (124) |
| 3 | 20 | 0.0048 (122) |

TABLE 3

Swell and Extractables Results

| Example | CNC (Weight %) | Swell (%) | Extractables (grams) | Extractables (%) |
|---|---|---|---|---|
| C1 | 0 | 3.2 | 0.0010 | 1.0 |
| 1 | 4 | 4.5 | 0.0011 | 1.1 |
| 2 | 10 | 13.1 | 0.0009 | 0.9 |
| 3 | 20 | 26.8 | 0.0004 | 0.4 |
| Backing Only | | 37.5 | 0.0002 | 0.6 |

TABLE 4

Peel Adhesion Strength Results (Stainless Steel)

| Example | CNC (Weight %) | Peel Adhesion Strength oz/in. (N/dm) Dry | Wet | % Retention vs C1 Dry | Wet |
|---|---|---|---|---|---|
| C1 | 0 | 11.0 (12.1) | 10.1 (11.1) | 100 | 100 |
| 1 | 4 | 12.0 (13.1) | 10.1 (11.0) | 109 | 99 |
| 2 | 10 | 12.5 (13.7) | 10.3 (11.3) | 114 | 101 |
| 3 | 20 | 12.6 (13.8) | 11.1 (12.2) | 114 | 110 |

Table 4 shows that Examples 1-3 exhibit similar or improved peel adhesion properties (dry and wet) with respect to Comparative Example 1. Further, Example 3 exhibits a wet peel adhesion strength that is as good as the dry peel adhesion strength of Comparative Example 1.

TABLE 5

Shear Adhesion Strength (Stainless Steel)

| Example | CNC (Weight %) | Time (minutes) | % Retention vs C1 |
|---|---|---|---|
| C1 | 0 | 518 | 100 |
| 1 | 4 | 506 | 98 |
| 2 | 10 | 989 | 191 |
| 3 | 20 | 1085 | 209 |

For comparative example C1 and Examples 1-3, the swell data demonstrate the increase in water uptake that results with increased concentration of CNC in the adhesive. This happens without increasing the extractables of the material throughout the soak procedure. Additionally, the wet peel adhesion force approaches the dry peel adhesion force of the dry comparative example, C1, as the CNC content reaches 20 wt % (Example 3). This happens without compromising the shear performance of the material at room temperature.

Example 4 and Comparative Example 2 (C2)

A polydiorganosiloxane-polyoxamide block copolymer (SiOxCp) adhesive was provided as described above. Compositions containing the materials and amounts shown in Table 6 were prepared by mixing the materials in a cup using a centrifugal resin mixer (MAX 40 mixing cup and a Model DAC 150.1 FVZ-K SPEEDMIXER) at 1000 rpm for one minute then at 2000 rpm for one minute to ensure a uniform dispersion was obtained. The CNC component was added as a solid powder.

TABLE 6

Compositions

| Example | SiOxCp Solution (grams) | SiOxCp Solids (grams) | CNC (grams) | CNC (Weight %) |
|---|---|---|---|---|
| C2 | 30.00 | 10.50 | 0.00 | 0 |
| 4 | 30.00 | 10.50 | 1.22 | 10 |

The compositions shown in Table 6 were then coated onto the thermoplastic elastomer side of Backing Film 1 using a knife-over-bed coating station with a gap setting of 0.008 inches (203 micrometers) greater than the thickness of Backing Film 1. The coated Backing Film 1 was dried at 70° C. for 30 minutes and stored at 74° F. (23.3° C.) and 50% RH for at least 24 hours before evaluation as described in the test methods. The results are shown below in Tables 7-10.

TABLE 7

Thickness Results

| Example | CNC (Weight %) | Thickness inches (micrometers) |
|---|---|---|
| C2 | 0 | 0.0022 (56) |
| 4 | 10 | 0.0023 (58) |

TABLE 8

Swell and Extractables Results

| Example | CNC (Weight %) | Swell (%) | Extractables (grams) | Extractables (%) |
|---|---|---|---|---|
| C2 | 0 | 6.6 | 0.0006 | 0.9 |
| 4 | 10 | 19.7 | 0.0008 | 1.2 |
| Backing Only | | 57.7 | 0.0004 | 1.3 |

TABLE 9

Peel Adhesion Strength Results (Polypropylene)

| | | Peel Adhesion Strength oz/in. (N/dm) | | % Retention vs C2 | |
|---|---|---|---|---|---|
| Example | CNC (Weight %) | Dry | Wet | Dry | Wet |
| C2 | 0 | 41.1 (45.0) | 37.3 (40.8) | 100 | 100 |
| 4 | 10 | 31.7 (34.7) | 27.2 (29.8) | 73 | 77 |

TABLE 10

Shear Adhesion Strength - Method A (Polypropylene)

| | | Time (minutes) | | % Retention vs C2 | |
|---|---|---|---|---|---|
| Example | CNC (Weight %) | 250 grams | 500 grams | 250 grams | 500 grams |
| C2 | 0 | 10,000+ | 10,000+ | 100 | 100 |
| 4 | 10 | 10,000+ | 10,000+ | 100 | 100 |

For comparative example C2 and example 4, the swell data continue to demonstrate the improvement of water uptake capabilities with the addition of CNCs to the silicone PSA system. The room temperature shears on polypropylene passed 10,000 minutes at a 0.5 inch×1 inch overlap with both 250 and 500 gram weights. Additionally, the peel performance under both wet and dry conditions demonstrates that the processed material is an adhesive.

Examples 5-7 and Comparative Example 3 (C3)

A silicone-polyurea copolymer (SPUCp)-based pressure sensitive adhesive was provided as described above. Compositions containing the materials and amounts shown in Table 11 were prepared by mixing the materials in a cup using a centrifugal resin mixer (MAX 40 mixing cup and a Model DAC 150.1 FVZ-K SPEEDMIXER) at 1000 rpm for one minute then at 2000 rpm for one minute to ensure a uniform dispersion was obtained. The CNC component was added as a solid powder.

TABLE 11

Compositions

| Example | SPUCp Solution (grams) | SPUCp Solids (grams) | CNC (grams) | CNC (Weight %) |
|---|---|---|---|---|
| C3 | 40.00 | 12.00 | 0.00 | 0 |
| 5 | 40.00 | 12.00 | 0.06 | 0.5 |
| 6 | 40.00 | 12.00 | 0.12 | 1 |
| 7 | 40.00 | 12.00 | 0.25 | 2 |

The compositions shown in Table 11 were then coated onto the coated side of Backing Film 1 using a knife-over-bed coating station with a gap setting of 0.008 inches (203 micrometers) greater than the thickness of Backing Film 1. The coated Backing Film 1 was dried at 70° C. for 30 minutes and stored at 74° F. (23.3° C.) and 50% RH for at least 24 hours before evaluation as described in the test methods. The results are shown below in Tables 12-15.

TABLE 12

Thickness Results

| Example | CNC (Weight %) | Thickness inches (micrometers) |
|---|---|---|
| C3 | 0 | 0.0019 (48) |
| 5 | 0.5 | 0.0019 (48) |
| 6 | 1 | 0.0021 (53) |
| 7 | 2 | 0.0019 (48) |

TABLE 13

Swell and Extractable Results

| Example | CNC (Weight %) | Swell (%) | Extractables (grams) | Extractables (%) |
|---|---|---|---|---|
| C3 | 0 | 17.0 | 0.0002 | 0.3 |
| 5 | 0.5 | 35.8 | 0.0004 | 0.8 |
| 6 | 1 | 27.8 | 0.0006 | 1.1 |
| 7 | 2 | 36.5 | 0.0004 | 0.7 |
| Backing Only | | 52.3 | 0.0008 | 2.3 |

TABLE 14

Peel Adhesion Strength Results (Polypropylene)

| Example | CNC (Weight %) | Peel Adhesion Strength oz/in (N/dm) | % Retention vs C3 |
|---|---|---|---|
| C3 | 0 | 17.8 (19.5) | 100 |
| 5 | 0.5 | 23.6 (25.8) | 133 |
| 6 | 1 | 18.6 (20.4) | 104 |

TABLE 14-continued

Peel Adhesion Strength Results (Polypropylene)

| Example | CNC (Weight %) | Peel Adhesion Strength oz/in (N/dm) | % Retention vs C3 |
|---|---|---|---|
| 7 | 2 | 18.2 (19.9) | 102 |

TABLE 15

Shear Adhesion Strength - Method B (Polypropylene)

| Example | CNC (Weight %) | Time (minutes) | % Retention vs C3 |
|---|---|---|---|
| C3 | 0 | 10,000+ | 100 |
| 5 | 0.5 | 10,000+ | 100 |
| 6 | 1 | 10,000+ | 100 |
| 7 | 2 | 10,000+ | 100 |

For comparative example C3 and Examples 5-7, the addition of CNC results in increased water uptake for all concentrations. The room temperature shears on polypropylene passed 10,000 minutes at a 0.5 inch×1 inch overlap with 100 gram weights. Additionally, the peel performance demonstrates that the processed material is an adhesive.

Examples 8-10 and Comparative Example 4 (C4)

Compositions containing the materials and amounts shown in Table 16 were prepared by mixing the materials in a cup using a centrifugal resin mixer (MAX 40 mixing cup and a Model DAC 150.1 FVZ-K SPEEDMIXER) at 1000 rpm for one minute then at 2000 rpm for one minute to ensure a uniform dispersion was obtained. The CNC component was added as a solid powder.

TABLE 16

Compositions

| Example | BIO-PSA Solution (grams) | BIO-PSA Solids (grams) | CNC (grams) | CNC (Weight %) |
|---|---|---|---|---|
| C4 | 30.00 | 18.48 | 0.00 | 0 |
| 8 | 30.00 | 18.48 | 0.38 | 2 |
| 9 | 30.00 | 18.48 | 0.98 | 5 |
| 10 | 30.00 | 18.48 | 2.06 | 10 |

The compositions shown in Table 16 were then coated onto the primed side of Backing Film 2 using a knife-over-bed coating station with a gap setting of 0.006 inches (152 micrometers) greater than the thickness of Backing Film 2. The coated Backing Film 2 was dried at 70° C. for 30 minutes and stored at 74° F. (23.3° C.) and 50% RH for at least 24 hours before evaluation as described in the test methods. The results are shown below in Tables 17-20.

TABLE 17

Thickness Results

| Example | CNC (Weight %) | Thickness inches (micrometers) |
|---|---|---|
| C4 | 0 | 0.0021 (53) |
| 8 | 2 | 0.0021 (53) |
| 9 | 5 | 0.0023 (58) |
| 10 | 10 | 0.0023 (58) |

TABLE 18

Swell and Extractables Results

| Example | CNC (Weight %) | Swell (%) | Extractables (grams) | Extractables (%) |
|---|---|---|---|---|
| C4 | 0 | 0.4 | 0.0003 | 0.4 |
| 8 | 2 | 4.7 | 0.0001 | 0.2 |
| 9 | 5 | 8.6 | 0.0002 | 0.3 |
| 10 | 10 | 13.4 | −0.0001* | −0.1* |
| Backing Only | | 0.1 | 0.0001 | 0.0 |

*within error limits of measurement

TABLE 19

Peel Adhesion Strength Results (Stainless Steel)

| Example | CNC (Weight %) | Peel Adhesion Strength oz/in. (N/dm) Dry | Peel Adhesion Strength oz/in. (N/dm) Wet | % Retention vs C4 Dry | % Retention vs C4 Wet |
|---|---|---|---|---|---|
| C4 | 0 | 56.3 (61.6) | 44.9 (49.2) | 100 | 100 |
| 8 | 2 | 52.4 (57.4) | 38.5 (42.1) | 93 | 86 |
| 9 | 5 | 47.3 (51.8) | 34.1 (37.4) | 84 | 76 |
| 10 | 10 | 39.1 (42.8) | 29.2 (32.0) | 69 | 65 |

TABLE 20

Shear Adhesion Strength (Stainless Steel)

| Example | CNC Weight % | Time (minutes) | % Retention vs C4 |
|---|---|---|---|
| C4 | 0 | 2928 | 100 |
| 8 | 2 | 3052 | 104 |
| 9 | 5 | 3411 | 116 |
| 10 | 10 | 4023 | 137 |

For comparative example C4 and Examples 8-10, the addition of CNC results in increased water uptake for all concentrations tested. The peel performance under both wet and dry conditions demonstrates that the resulting material is an adhesive. Additionally, the room temperature shear performance on stainless steel consistently increased with increasing concentration of CNCs in the silicone matrix at a 1 inch×1 inch overlap with 250 gram weights.

All of the patents and patent applications mentioned above are hereby expressly incorporated by reference. The embodiments described above are illustrative of the present invention and other constructions are also possible. Accordingly, the present disclosure should not be deemed limited to the embodiments described in detail above and shown in the accompanying drawings, but instead only by a fair scope of the claims that follow along with their equivalents.

What is claimed is:

1. An adhesive composition comprising:
   a silicone-based adhesive, wherein the silicone-based adhesive comprises a silicone polyurea block copolymer, a polydiorganosiloxane polyoxamide block copolymer, or a combination thereof; and
   cellulose nanocrystals dispersed in the silicone-based adhesive.

2. The adhesive composition of claim 1, wherein the silicone-based adhesive comprises a polydiorganosiloxane.

3. The adhesive composition of claim 1, wherein the silicone-based adhesive comprises polydimethylsiloxane.

4. The adhesive composition of claim 1, wherein the cellulose nanocrystals are present in an amount of 0.5 to 20 weight percent, 0.5 to 9 weight percent, or 10 to 20 weight percent of the total adhesive composition.

5. The adhesive composition of claim 1, wherein the cellulose nanocrystals are not surface modified.

6. The adhesive composition of claim 1, wherein the adhesive composition exhibits a wet peel adhesion on stainless steel that is no less than 70%, 80%, or 90% of the wet peel adhesion of the same composition without the cellulose nanocrystals, as determined by a Wet Peel Adhesion Strength Test.

7. The adhesive composition of claim 1, wherein the adhesive composition exhibits a dry peel adhesion on stainless steel that is no less than 70%, 80%, or 90% of the dry peel adhesion of the same composition without the cellulose nanocrystals, as determined by a Dry Peel Adhesion Strength Test.

8. The adhesive composition of claim 1, wherein the adhesive composition exhibits a room temperature shear of greater than 10,000 minutes or of no less than 90% of the room temperature shear of the same composition without the cellulose nanocrystals, as determined by a Shear Adhesion Strength Test-Polypropylene (Method A) or a Shear Adhesion Strength Test-Polypropylene (Method B) at room temperature.

9. The adhesive composition of claim 1, wherein the adhesive composition exhibits a room temperature shear of greater than 10,000 minutes or of no less than 90% of the room temperature shear of the same composition without the cellulose nanocrystals, as determined by a Shear Adhesion Strength Test-Stainless Steel at room temperature.

10. The adhesive composition of claim 1, wherein the adhesive composition exhibits a swell of at least 4%, as determined by a Swell Test.

11. The adhesive composition of claim 1, wherein less than 2 weight percent of the cellulose nanocrystals are extractable from the adhesive composition, as determined by a % Extractables Test.

12. An article comprising a substrate and a layer of the adhesive composition according to claim 1 adhered to the substrate.

13. The article of claim 12, wherein the layer of adhesive composition has a thickness of 20 micrometers to 300 micrometers.

14. A method of making an adhesive composition, the method comprising:
   mixing cellulose nanocrystals in a silicone-based adhesive to disperse the cellulose nanocrystals, wherein the silicone-based adhesive comprises a silicone polyurea block copolymer, a polydiorganosiloxane polyoxamide block copolymer, or a combination thereof.

15. A method of making an article, the method comprising disposing a layer of the adhesive composition of claim 1 on a substrate, wherein the method further comprises exposing the layer of the adhesive composition to actinic radiation.

16. The method of claim 15, wherein the actinic radiation comprises e-beam radiation.

* * * * *